(12) United States Patent
Lohse et al.

(10) Patent No.: US 8,198,450 B2
(45) Date of Patent: Jun. 12, 2012

(54) QUINOLINONE DERIVATIVES AND THEIR PHARMACEUTICAL COMPOSITIONS

(75) Inventors: Olivier Lohse, Rixheim (FR); Stephanie Monnier, Raedersheim (FR); Jean-Louis Reber, Kembs (FR)

(73) Assignee: Novartis AG, Basel (CH)

( * ) Notice: Subject to any disclaimer, the term of this patent is extended or adjusted under 35 U.S.C. 154(b) by 551 days.

(21) Appl. No.: 12/304,617

(22) PCT Filed: Jul. 2, 2007

(86) PCT No.: PCT/EP2007/056632
§ 371 (c)(1),
(2), (4) Date: Dec. 12, 2008

(87) PCT Pub. No.: WO2008/000839
PCT Pub. Date: Jan. 3, 2008

(65) Prior Publication Data
US 2009/0325912 A1 Dec. 31, 2009

(30) Foreign Application Priority Data

| | | | |
|---|---|---|---|
| Jun. 30, 2006 | (GB) | | 0613156.9 |
| Jun. 30, 2006 | (GB) | | 0613158.5 |
| Jun. 30, 2006 | (GB) | | 0613159.3 |
| Jun. 30, 2006 | (GB) | | 0613160.1 |
| Jul. 13, 2006 | (EP) | | 06 117129 |

(51) Int. Cl.
*C07D 215/00* (2006.01)
*A61K 31/47* (2006.01)
(52) U.S. Cl. ........................ 546/157; 514/312
(58) Field of Classification Search ........................ None
See application file for complete search history.

(56) References Cited

U.S. PATENT DOCUMENTS

| | | | |
|---|---|---|---|
| 2004/0010003 A1 | 1/2004 | Banholzer et al. | |
| 2004/0132759 A1 | 7/2004 | Konetzki et al. | |

FOREIGN PATENT DOCUMENTS

| | | |
|---|---|---|
| JP | 2005/343889 | 12/2005 |
| WO | 00/75114 | 12/2000 |
| WO | 02/45703 | 6/2002 |
| WO | 02/066481 | 8/2002 |
| WO | 03/042211 | 5/2003 |
| WO | 2004/074290 | 9/2004 |
| WO | 2004/076422 | 9/2004 |
| WO | 2004/087142 | 10/2004 |
| WO | 2004/087668 | 10/2004 |
| WO | 2005/110402 | 11/2005 |
| WO | 2005/123684 | 12/2005 |
| WO | 2006/102194 | 9/2006 |
| WO | 2006/128674 | 12/2006 |
| WO | 2007/013673 | 2/2007 |

OTHER PUBLICATIONS

Brittain, H., ed Polymorphism in Pharmaceutical Solids Informa Healthcare USA 2009, p. 334.*
Davies et al. "Indacaterol". Drugs of the Future, vol. 30, No. 12, pp. 1219-1224 (2005).
Bullock, A.N et al. Structural Basis of Inhibitor Specificity of the Human Protooncogene Proviral Insertin Site in Moloney Murine Leukemia Virus (PIM-1) Kinase, Journal of Medicinal Chemistry, vol. 48, No. 24 , pp. 7604-7614 (2005).
Callahan, J.F et al. "Identification of Novel Inhibitors of the Transforming Growth Factor beta-1 (TGF-beta-1) type 1 receptor (ALK5)", Journal of Medicinal Chemistry, voo. 45, No. 5, pp. 999-1001 (2002).
Berge S.M. et al., "Pharmaceutical Salts", Journal of Pharmaceutical Sciences, 66(1):1-19 1977.
H.G. Brittain et al., Polymorphisms in pharmaceutical solids, David J Grant "Theory and Origin of Polymorphism", Chap 1, pp. 1-10, and J. K. Guillory Chapter 5, "Generation of Polymorphs, Hydrates, Solvates, and Amorphous Solids", pp. 183-226 1999.

* cited by examiner

*Primary Examiner* — Janet Andres
*Assistant Examiner* — Heidi Reese
(74) *Attorney, Agent, or Firm* — Cozette M McAvoy

(57) ABSTRACT

Compounds of formula I

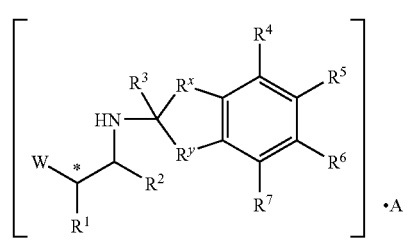

in salt or solvate form, wherein W, $R^x$, $R^y$, $R^1$, $R^2$, $R^3$, $R^4$, $R^5$, $R^6$ and $R^7$ and A have the meanings as indicated in the specification, are useful for treating diseases mediated by the $\beta_2$-adrenoreceptor. Pharmaceutical compositions that contain the compounds and processes for preparing the compounds are also described.

16 Claims, 4 Drawing Sheets

QUINOLINONE DERIVATIVES AND THEIR PHARMACEUTICAL COMPOSITIONS

Figure 1:
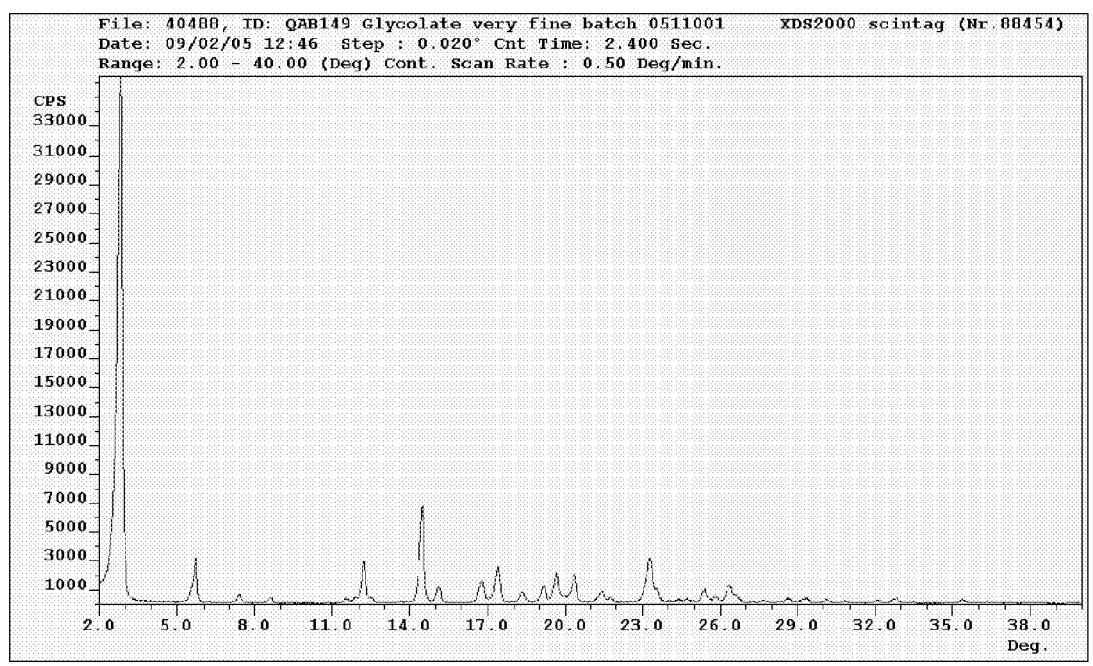

This invention relates to novel salts, a process for their preparation and their use in pharmaceutical compositions.

In a first aspect, the present invention provides a compound of formula I

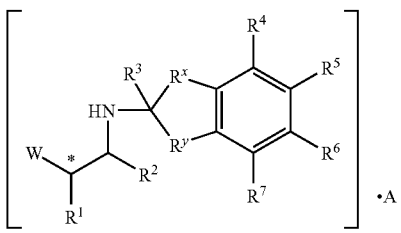

in salt or solvate form,
where W is a group of formula

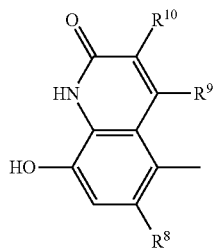

$R^x$ and $R^y$ are both —$CH_2$— or —$(CH_2)_2$—;
$R^1$ is hydrogen, hydroxy, or $C_1$-$C_{10}$-alkoxy;
$R^2$ and $R^3$ are each independently hydrogen or $C_1$-$C_{10}$-alkyl;
$R^4$, $R^5$, $R^6$ and $R^7$ are each independently hydrogen, halogen, cyano, hydroxy, $C_1$-$C_{10}$-alkoxy, $C_6$-$C_{10}$-aryl, $C_1$-$C_{10}$-alkyl, $C_1$-$C_{10}$-alkyl substituted by one or more halogen atoms or one or more hydroxy or $C_1$-$C_{10}$-alkoxy groups, $C_1$-$C_{10}$-alkyl interrupted by one or more hetero atoms, $C_2$-$C_{10}$-alkenyl, trialkylsilyl, carboxy, $C_1$-$C_{10}$-alkoxycarbonyl, or —$CONR^{11}R^{12}$ where $R^{11}$ and $R^{12}$ are each independently hydrogen or $C_1$-$C_{10}$-alkyl,
or $R^4$ and $R^5$, $R^5$ and $R^6$, or $R^6$ and $R^7$ together with the carbon atoms to which they are attached denote a 5-, 6- or 7-membered carbocyclic ring or a 4- to 10-membered heterocyclic ring;
$R^8$, $R^9$ and $R^{10}$ are each independently hydrogen or $C_1$-$C_4$-alkyl; and
A is selected from the group consisting of hydrogen succinate, fumarate, hippurate, mesylate, hydrogen sulphate, hydrogen tartrate, hydrogen chloride, hydrogen bromide, formate, esylate, tosylate, glycolate, acetate, xinafoate and hydrogen malonate.

Terms used in the specification have the following meanings:

"Halogen" or "halo" as used herein denotes a element belonging to group 17 (formerly group VII) of the Periodic Table of Elements, which may be, for example, fluorine, chlorine, bromine or iodine. Preferably halo or halogen is fluorine or chlorine.

"$C_1$-$C_{10}$-alkyl" as used herein denotes straight chain or branched alkyl that contains one to ten carbon atoms. Preferably, $C_1$-$C_{10}$-alkyl is $C_1$-$C_4$-alkyl.

"Alkyl interrupted by one or more hetero atoms" denotes straight chain or branched alkyl e.g. $C_2$ to $C_{10}$ alkyl, in which one or more pairs of carbon atoms are linked by —O—, —NR—, —S—, —S(=O)— or —$SO_2$—, where R is hydrogen or $C_1$ to $C_{10}$ (preferably $C_1$ to $C_4$) alkyl. Preferred such groups are alkoxyalkyl groups, preferably $C_1$-$C_4$-alkoxy-$C_1$-$C_4$-alkyl groups.

"$C_2$-$C_{10}$-alkenyl" as used herein denotes straight chain or branched hydrocarbon chains that contain two to ten carbon atoms and one or more carbon-carbon double bonds. Preferably "$C_2$-$C_{10}$-alkenyl" is "$C_2$-$C_4$-alkenyl".

"5-, 6 or 7-membered carbocyclic ring" as used herein denotes a carbocyclic group having 5 to 7 ring carbon atoms, either cycloaliphatic, such as a $C_3$-$C_7$-cycloalkyl, or aromatic, such as phenyl, which can be substituted by one or more, usually one or two, $C_1$-$C_4$-alkyl groups.

"$C_5$-$C_7$-cycloalkyl" as used herein denotes cycloalkyl having 5 to 7 ring carbon atoms, for example cyclopentyl, cyclohexyl or cycloheptyl, any of which can be substituted by one or more, usually one or two, $C_1$-$C_4$-alkyl groups.

"$C_1$-$C_{10}$-alkoxy" as used herein denotes straight chain or branched alkoxy that contains 1 to 10 carbon atoms. Preferably, $C_1$-$C_{10}$-alkoxy is $C_1$-$C_4$-alkoxy.

"$C_1$-$C_{10}$-alkoxycarbonyl" as used herein denotes $C_1$-$C_{10}$-alkoxy as hereinbefore defined linked through an oxygen atom thereof to a carbonyl group.

"$C_6$-$C_{10}$-aryl" as used herein denotes a monovalent carbocyclic aromatic group that contains 6 to 10 carbon atoms and which may be, for example, a monocyclic group such as phenyl or a bicyclic group such as naphthyl. Preferably $C_6$-$C_{10}$-aryl is $C_6$-$C_8$-aryl, especially phenyl.

"4- to 10-membered heterocyclic ring having at least one ring nitrogen, oxygen or sulphur atom" as used herein may be, for example, pyrrole, pyrrolidine, pyrazole, imidazole, triazole, tetrazole, thiadiazole, oxazole, isoxazole, thiophene, thiazole, isothiazole, oxadiazole, pyridine, pyrazine, pyridazine, pyrimidine, piperidine, piperazine, triazine, oxazine, morpholino, quinoline, isoquinoline, naphthyridine, indane or indene. Preferred heterocyclic rings include thiazole, pyrrolidine, piperidine, azacycloheptane and isoxazole.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

Preferred compounds of formula I include those wherein $R^8$, $R^9$ and $R^{10}$ are each H, $R^1$ is OH, $R^2$ and $R^3$ are each H and
(i) $R^x$ and $R^y$ are both —$CH_2$—, and $R^4$ and $R^7$ are each $CH_3O$— and $R^5$ and $R^6$ are each H;
(ii) $R^x$ and $R^y$ are both —$CH_2$—, and $R^4$ and $R^7$ are each H and $R^5$ and $R^6$ are each $CH_3CH_2$—;
(iii) $R^x$ and $R^y$ are both —$CH_2$—, and $R^4$ and $R^7$ are each H and $R^5$ and $R^6$ are each $CH_3$—;
(iv) $R^x$ and $R^y$ are both —$CH_2$—, and $R^4$ and $R^7$ are each $CH_3CH_2$— and $R^5$ and $R^6$ are each H;
(v) $R^x$ and $R^y$ are both —$CH_2$—, and $R^4$ and $R^7$ are each H and $R^5$ and $R^6$ together denote —$(CH_2)_4$—;
(vi) $R^x$ and $R^y$ are both —$CH_2$—, and $R^4$ and $R^7$ are each H and $R^5$ and $R^6$ together denote —$O(CH_2)_2O$—;
(vii) $R^x$ and $R^y$ are both —$CH_2$—, and $R^4$ and $R^7$ are each H and $R^5$ and $R^6$ are each $CH_3(CH_2)_3$—;
(viii) $R^x$ and $R^y$ are both —$CH_2$—, and $R^4$ and $R^7$ are each H and $R^5$ and $R^6$ are each $CH_3(CH_2)_2$—;
(ix) $R^x$ and $R^y$ are both —$(CH_2)_2$—, $R^4$, $R^5$, $R^6$ and $R^7$ are each H; or (x) $R^x$ and $R^y$ are both —CH$_2$—, and $R^4$ and $R^7$ are each H and $R^5$ and $R^6$ are each CH$_3$OCH$_2$—.

Preferred compounds of formula I include namely: 8-hydroxy-5-[1-hydroxy-2-(indan-2-ylamino)-ethyl]-1H-quinolin-2-one glycolate, 5-[2-(5,6-dimethoxy-indan-2-ylamino)-1-hydroxy-ethyl]-8-hydroxy-1H-quinolin-2-one glycolate, 5-[2-(5,6-diethyl-indan-2-ylamino)-1-hydroxy-ethyl]-8-hydroxy-3-methyl-1H-quinolin-2-one glycolate, 5-[2-(5,6-diethyl-indan-2-ylamino)-1-hydroxy-ethyl]-8-methoxy-methoxy-6-methyl-1H-quinolin-2-one glycolate, 5-[2-(5,6-diethyl-indan-2-ylamino)-1-hydroxy-ethyl]-8-hydroxy-6-methyl-1H-quinolin-2-one glycolate, 8-hydroxy-5-[2-(5,6-diethyl-indan-2-ylamino)-1-hydroxy-ethyl]-3,4-dihydro-1H-quinolin-2-one glycolate, 5-[(R)-2-(5,6-diethyl-2-methyl-indan-2-ylamino)-1-hydroxy-ethyl]-8-hydroxy-1H-quinolin-2-one glycolate, (S)-5-[2-(4,7-diethyl-indan-2-ylamino)-1-hydroxy-ethyl]-8-hydroxy-1H-quinolin-2-one hydrochloride glycolate; 5-[(R)-1-hydroxy-2-(6,7,8,9-tetrahydro-5H-benzocyclohepten-7-ylamino)-ethyl]-8-hydroxy-1H-quinolin-2-one hydrochloride glycolate, (R)-5-[2-(5,6-diethyl-indan-2-ylamino)-1-hydroxy-ethyl]-8-hydroxy-1H-quinolin-2-one maleate glycolate, (R)-5-[2-(5,6-diethyl-indan-2-ylamino)-1-hydroxy-ethyl]-8-hydroxy-1H-quinolin-2-one hydrochloride glycolate, (R)-8-hydroxy-5-[(S)-1-hydroxy-2-(4,5,6,7-tetramethyl-indan-2-ylamino)-ethyl]-1H-quinolin-2-one glycolate, 8-hydroxy-5-[(R)-1-hydroxy-2-(2-methyl-indan-2-ylamino)-ethyl]-1H-quinolin-2-one glycolate, 5-[2-(5,6-diethyl-indan-2-ylamino)-ethyl]-8-hydroxy-1H-quinolin-2-one glycolate, 8-hydroxy-5-[(R)-1-hydroxy-2-(2-methyl-2,3,5,6,7,8-hexahydro-1H-cyclopenta[b]naphthalen-2-ylamino)-ethyl]-1H-quinolin-2-one glycolate, 5-[(S)-2-(2,3,5,6,7,8-hexahydro-1H-cyclopenta-[b]naph-thalen-2-ylamino)-1-hydroxy-ethyl]-8-hydroxy-1H-quinolin-2-one glycolate, 8-hydroxy-5-[1-hydroxy-2-(indan-2-ylamino)-ethyl]-1H-quinolin-2-one acetate, 5-[2-(5,6-dimethoxy-indan-2-ylamino)-1-hydroxy-ethyl]-8-hydroxy-1H-quinolin-2-one acetate, 5-[2-(5,6-diethyl-indan-2-ylamino)-1-hydroxy-ethyl]-8-hydroxy-3-methyl-1H-quinolin-2-one acetate, 5-[2-(5,6-diethyl-indan-2-ylamino)-1-hydroxy-ethyl]-8-methoxy-methoxy-6-methyl-1H-quinolin-2-one acetate, 5-[2-(5,6-diethyl-indan-2-ylamino)-1-hydroxy-ethyl]-8-hydroxy-6-methyl-1H-quinolin-2-one acetate, 8-hydroxy-5-[2-(5,6-diethyl-indan-2-ylamino)-1-hydroxy-ethyl]-3,4-dihydro-1H-quinolin-2-one acetate, 5-[(R)-2-(5,6-diethyl-2-methyl-indan-2-ylamino)-1-hydroxy-ethyl]-8-hydroxy-1H-quinolin-2-one acetate, (S)-5-[2-(4,7-diethyl-indan-2-ylamino)-1-hydroxy-ethyl]-8-hydroxy-1H-quinolin-2-one hydrochloride acetate, 5-[(R)-1-hydroxy-2-(6,7,8,9-tetrahydro-5H-benzocyclohepten-7-ylamino)-ethyl]-8-hydroxy-1H-quinolin-2-one hydrochloride acetate, (R)-5-[2-(5,6-diethyl-indan-2-ylamino)-1-hydroxy-ethyl]-8-hydroxy-1H-quinolin-2-one maleate acetate, (R)-5-[2-(5,6-diethyl-indan-2-ylamino)-1-hydroxy-ethyl]-8-hydroxy-1H-quinolin-2-one hydrochloride acetate, (R)-8-hydroxy-5-[(S)-1-hydroxy-2-(4,5,6,7-tetramethyl-indan-2-ylamino)-ethyl]-1H-quinolin-2-one acetate, 8-hydroxy-5-[(R)-1-hydroxy-2-(2-methyl-indan-2-ylamino)-ethyl]-1H-quinolin-2-one acetate, 5-[2-(5,6-diethyl-indan-2-ylamino)-ethyl]-8-hydroxy-1H-quinolin-2-one acetate, 8-hydroxy-5-[(R)-1-hydroxy-2-(2-methyl-2,3,5,6,7,8-hexahydro-1H-cyclopenta[b]naphthalen-2-ylamino)-ethyl]-1H-quinolin-2-one acetate, 5-[(S)-2-(2,3,5,6,7,8-hexahydro-1H-cyclopenta[b]naph-thalen-2-ylamino)-1-hydroxy-ethyl]-8-hydroxy-1H-quinolin-2-one acetate, 8-hydroxy-5-[1-hydroxy-2-(indan-2-ylamino)-ethyl]-1H-quinolin-2-one xinafoate, 5-[2-(5,6-dimethoxy-indan-2-ylamino)-1-hydroxy-ethyl]-8-hydroxy-1H-quinolin-2-one xinafoate, 5-[2-(5,6-diethyl-indan-2-ylamino)-1-hydroxy-ethyl]-8-hydroxy-3-methyl-1H-quinolin-2-one xinafoate, 5-[2-(5,6-diethyl-indan-2-ylamino)-1-hydroxy-ethyl]-8-methoxy-methoxy-6-methyl-1H-quinolin-2-one xinafoate, 5-[2-(5,6-diethyl-indan-2-ylamino)-1-hydroxy-ethyl]-8-hydroxy-6-methyl-1H-quinolin-2-one xinafoate, 8-hydroxy-5-[2-(5,6-diethyl-indan-2-ylamino)-1-hydroxy-ethyl]-3,4-dihydro-1H-quinolin-2-one xinafoate, 5-[(R)-2-(5,6-diethyl-2-methyl-indan-2-ylamino)-1-hydroxy-ethyl]-8-hydroxy-1H-quinolin-2-one xinafoate, (S)-5-[2-(4,7-diethyl-indan-2-ylamino)-1-hydroxy-ethyl]-8-hydroxy-1H-quinolin-2-one hydrochloride xinafoate, 5-[(R)-1-hydroxy-2-(6,7,8,9-tetrahydro-5H-benzocyclohepten-7-ylamino)-ethyl]-8-hydroxy-1H-quinolin-2-one hydrochloride xinafoate, (R)-5-[2-(5,6-diethyl-indan-2-ylamino)-1-hydroxy-ethyl]-8-hydroxy-1H-quinolin-2-one maleate xinafoate, (R)-5-[2-(5,6-diethyl-indan-2-ylamino)-1-hydroxy-ethyl]-8-hydroxy-1H-quinolin-2-one hydrochloride xinafoate, (R)-8-hydroxy-5-[(S)-1-hydroxy-2-(4,5,6,7-tetramethyl-indan-2-ylamino)-ethyl]-1H-quinolin-2-one xinafoate, 8-hydroxy-5-[(R)-1-hydroxy-2-(2-methyl-indan-2-ylamino)-ethyl]-1H-quinolin-2-one xinafoate, 5-[2-(5,6-diethyl-indan-2-ylamino)-ethyl]-8-hydroxy-1H-quinolin-2-one xinafoate, 8-hydroxy-5-[(R)-1-hydroxy-2-(2-methyl-2,3,5,6,7,8-hexahydro-1H-cyclopenta[b]naphthalen-2-ylamino)-ethyl]-1H-quinolin-2-one xinafoate, 5-[(S)-2-(2,3,5,6,7,8-hexahydro-1H-cyclopenta[b]naph-thalen-2-ylamino)-1-hydroxy-ethyl]-8-hydroxy-1H-quinolin-2-one xinafoate, 8-hydroxy-5-[1-hydroxy-2-(indan-2-ylamino)-ethyl]-1H-quinolin-2-one hydrogen malonate, 5-[2-(5,6-dimethoxy-indan-2-ylamino)-1-hydroxy-ethyl]-8-hydroxy-1H-quinolin-2-one hydrogen malonate, 5-[2-(5,6-diethyl-indan-2-ylamino)-1-hydroxy-ethyl]-8-hydroxy-3-methyl-1H-quinolin-2-one hydrogen malonate, 5-[2-(5,6-diethyl-indan-2-ylamino)-1-hydroxy-ethyl]-8-methoxy-methoxy-6-methyl-1H-quinolin-2-one hydrogen malonate, 5-[2-(5,6-diethyl-indan-2-ylamino)-1-hydroxy-ethyl]-8-hydroxy-6-methyl-1H-quinolin-2-one hydrogen malonate, 8-hydroxy-5-[2-(5,6-diethyl-indan-2-ylamino)-1-hydroxy-ethyl]-3,4-dihydro-1H-quinolin-2-one hydrogen malonate, 5-[(R)-2-(5,6-diethyl-2-methyl-indan-2-ylamino)-1-hydroxy-ethyl]-8-hydroxy-1H-quinolin-2-one hydrogen malonate, (S)-5-[2-(4,7-diethyl-indan-2-ylamino)-1-hydroxy-ethyl]-8-hydroxy-1H-quinolin-2-one hydrochloride hydrogen malonate, 5-[(R)-1-hydroxy-2-(6,7,8,9-tetrahydro-5H-benzocyclohepten-7-ylamino)-ethyl]-8-hydroxy-1H-quinolin-2-one hydrochloride hydrogen malonate, (R)-5-[2-(5,6-diethyl-indan-2-ylamino)-1-hydroxy-ethyl]-8-hydroxy-1H-quinolin-2-one maleate hydrogen malonate, (R)-5-[2-(5,6-diethyl-indan-2-ylamino)-1-hydroxy-ethyl]-8-hydroxy-1H-quinolin-2-one hydrochloride hydrogen malonate, (R)-8-hydroxy-5-[(S)-1-hydroxy-2-(4,5,6,7-tetramethyl-indan-2-ylamino)-ethyl]-1H-quinolin-2-one hydrogen malonate, 8-hydroxy-5-[(R)-1-hydroxy-2-(2-methyl-indan-2-ylamino)-ethyl]-1H-quinolin-2-one hydrogen malonate, 5-[2-(5,6-diethyl-indan-2-ylamino)-ethyl]-8-hydroxy-1H-quinolin-2-one hydrogen malonate, 8-hydroxy-5-[(R)-1-hydroxy-2-(2-methyl-2,3,5,6,7,8-hexahydro-1H-cyclopenta[b]naphthalen-2-ylamino)-ethyl]-1H-quinolin-2-one hydrogen malonate, and 5-[(S)-2-(2,3,5,6,7,8-hexahydro-1H-cyclopenta[b]naph-thalen-2-ylamino)-1-hydroxy-ethyl]-8-hydroxy-1H-quinolin-2-one hydrogen malonate.

Especially preferred compounds of formula I are compounds of formula II

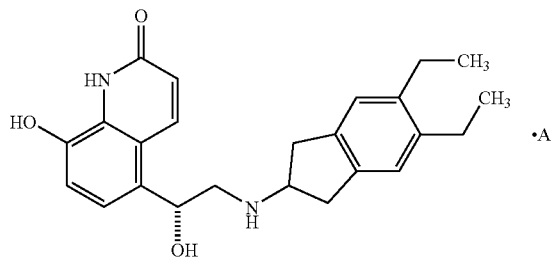

II where A is selected from the group consisting of hydrogen succinate, fumarate, hippurate, mesylate, hydrogen sulphate, hydrogen tartrate, hydrogen chloride, hydrogen bromide, formate, esylate, tosylate, glycolate, acetate, xinafoate and hydrogen malonate, namely (R)-5-[2-(5,6-diethyl-indan-2-ylamino)-1-hydroxyethyl]-8-hydroxy-1H-quinolin-2-one hydrogen succinate, (R)-5-[2-(5,6-diethyl-indan-2-ylamino)-1-hydroxyethyl]-8-hydroxy-1H-quinolin-2-one fumarate, (R)-5-[2-(5,6-diethyl-indan-2-ylamino)-1-hydroxyethyl]-8-hydroxy-1H-quinolin-2-one hippurate, (R)-5-[2-(5,6-diethyl-indan-2-ylamino)-1-hydroxyethyl]-8-hydroxy-1H-quinolin-2-one mesylate, (R)-5-[2-(5,6-diethyl-indan-2-ylamino)-1-hydroxyethyl]-8-hydroxy-1H-quinolin-2-one hydrogen sulfate, (R)-5-[2-(5,6-diethyl-indan-2-ylamino)-1-hydroxyethyl]-8-hydroxy-1H-quinolin-2-one hydrogen tartrate, (R)-5-[2-(5,6-diethyl-indan-2-ylamino)-1-hydroxyethyl]-8-hydroxy-1H-quinolin-2-one hydrogen chloride, (R)-5-[2-(5,6-diethyl-indan-2-ylamino)-1-hydroxyethyl]-8-hydroxy-1H-quinolin-2-one hydrogen bromide, (R)-5-[2-(5,6-diethyl-indan-2-ylamino)-1-hydroxyethyl]-8-hydroxy-1H-quinolin-2-one formate, (R)-5-[2-(5,6-diethyl-indan-2-ylamino)-1-hydroxyethyl]-8-hydroxy-1H-quinolin-2-one esylate, (R)-5-[2-(5,6-diethyl-indan-2-ylamino)-1-hydroxyethyl]-8-hydroxy-1H-quinolin-2-one tosylate, (R)-5-[2-(5,6-diethyl-indan-2-ylamino)-1-hydroxyethyl]-8-hydroxy-1H-quinolin-2-one glycolate, (R)-5-[2-(5,6-diethyl-indan-2-ylamino)-1-hydroxyethyl]-8-hydroxy-1H-quinolin-2-one acetate, (R)-5-[2-(5,6-diethyl-indan-2-ylamino)-1-hydroxyethyl]-8-hydroxy-1H-quinolin-2-one xinafoate and (R)-5-[2-(5,6-diethyl-indan-2-ylamino)-1-hydroxyethyl]-8-hydroxy-1H-quinolin-2-one hydrogen malonate.

The free form of compounds of formula I may be prepared by using the procedures described in international patent application WO 2000/075114, the contents of which is incorporated herein by reference. Compounds of formula I are prepared by reacting the free base with the relevant acid, or analogously as described in the Examples using processes known in the art for forming acid addition salts from secondary amines. When A is hydrogen succinate, fumarate, hippurate, mesylate, hydrogen sulphate, hydrogen tartrate, hydrogen chloride, hydrogen bromide, formate, esylate or tosylate the relevant acid is succinic acid, fumaric acid, hippuric acid, methanesulfonic acid, sulfuric acid, (+)-L-tartaric acid, hydrochloric acid, hydrobromic acid, formic acid, ethansulfonic acid and p-toluenesulfonic acid respectively. When A is glycolate, glycolate salts of the invention are prepared by reacting the free base with glycolic acid, or analogously as described in the Examples using processes known in the art for forming glycolic acid addition salts from secondary amines. When A is acetate, acetate salts of the invention are prepared by reacting the free base with acetic acid, or analogously as described in the Examples using processes known in the art for forming acetic acid addition salts from secondary amines. When A is xinafoate, xinafoate salts of the invention are prepared by reacting the free base with 1-hydroxy-2-naphthoic acid, or analogously as described in the Examples using processes known in the art for forming 1-hydroxy-2-naphthoic acid addition salts from secondary amines. When A is hydrogen malonate, hydrogen malonate salts of the invention are prepared by reacting the free base with malonic acid, or analogously as described in the Examples using processes known in the art for forming malonic acid addition salts from secondary amines.

In a second aspect the invention provides a pharmaceutical composition comprising, as active ingredient, an effective amount of a compound of formula I, optionally together with a pharmaceutically acceptable carrier. Preferably the composition is in inhalable form.

In a third aspect the invention concerns the use of a compound of formula I for the preparation of a medicament for the treatment of an inflammatory or obstructive airways disease.

In a fourth aspect the invention provides a process for preparing a compound of formula I comprising reacting the free base with the relevant acid.

Accordingly the process of the present invention comprises:
(i) for the preparation of compounds of formula I where A is hydrogen succinate, reacting the free base with succinic acid;
(ii) for the preparation of compounds of formula I where A is fumarate, reacting the free base with fumaric acid;
(iii) for the preparation of compounds of formula I where A is hippurate, reacting the free base with hippuric acid;
(iv) for the preparation of compounds of formula I where A is mesylate, reacting the free base with methanesulfonic acid;
(v) for the preparation of compounds of formula I where A is hydrogen sulphate, reacting the free base with sulfuric acid;
(vi) for the preparation of compounds of formula I where A is hydrogen tartrate, reacting the free base with (+)-L-tartaric;
(vii) for the preparation of compounds of formula I where A is hydrogen chloride, reacting the free base with hydrochloric acid;
(viii) for the preparation of compounds of formula I where A is hydrogen bromide, reacting the free base with hydrobromic acid;
(ix) for the preparation of compounds of formula I where A is formate, reacting the free base with formic acid;
(x) for the preparation of compounds of formula I where A is esylate, reacting the free base with ethansulfonic acid;
(xi) for the preparation of compounds of formula I where A is tosylate, reacting the free base with p-toluenesulfonic acid;
(xii) for the preparation of compounds of formula I where A is glycolate, reacting the free base with glycolic acid;
(xiii) for the preparation of compounds of formula I where A is acetate, reacting the free base with acetic acid;
(xiv) for the preparation of compounds of formula I where A is xinafoate, reacting the free base with 1-hydroxy-2-naphthoic acid; or
(xv) for the preparation of compounds of formula I where A is, hydrogen malonate, reacting the free base with malonic acid.

The compounds of formula I, hereinafter referred to alternatively as "agents of the invention", have good $\beta_2$-adrenoreceptor agonist activity and are useful as pharmaceuticals. The $\beta_2$-agonist activity, onset of action and duration of action of the agents of the invention may be tested using the guinea pig tracheal strip in vitro assay according to the procedure of R. A. Coleman and A. T. Nials, *J. Pharmacol. Methods* (1989), 21(1), 71-86. The binding potency and selectivity for the $\beta_2$-adrenoreceptor relative to the $\beta_1$-adrenoreceptor can be measured by a classical filtration binding assay according to the procedure of *Current Protocols in Pharmacology* (S. J. Enna (editor-in-chief) et al, John Wiley & Son, Inc, 1998), or by cAMP determination in cells expressing $\beta_2$- or $\beta_1$-adrenoceptor, according to the procedure of B. January et al, *British J. Pharmacol.* 123: 701-711 (1998).

The agents of the invention commonly have a rapid onset of action and have a prolonged stimulating action on the $\beta_2$-adrenoreceptor. They typically have Ki ($\beta_2$) values of the order of 0.1 to 1000 nM, durations of action of the order of 1 to greater than 12 hours or even 24 hours, and having binding selectivities for the $\beta_2$-adrenoreceptor relative to the $\beta_1$-adreno-receptor from 1.5 to 500.

Having regard to their $\beta_2$-agonist activity, the agents of the invention are suitable for use in the treatment of any condition which is prevented or alleviated by activation of the $\beta_2$-adreno-receptor. In view of their long acting selective $\beta_2$-agonist activity, the agents of the invention are useful in the relaxation of bronchial smooth muscle and the relief of bronchoconstriction. Relief of bronchoconstriction can be measured in models such as the in vivo plethysmography models of Chong et al, *J. Pharmacol. Toxicol. Methods* 1998, 39, 163-168, Hammelmann et al, *Am. J. Respir. Crit. Care Med.*, 1997, 156, 766-775 and analogous models. The agents of the invention are therefore useful in the treatment of obstructive or inflammatory airways diseases. In view of their long duration of action, it is possible to administer the agents of the invention once-a-day in the treatment of such diseases. In another aspect, agents of the invention commonly exhibit characteristics indicating a low incidence of side effects commonly encountered with $\beta_2$-agonists such as tachycardia, tremor and restlessness, such agents accordingly being suitable for use in on demand (rescue) treatment as well as prophylactic treatment of obstructive or inflammatory airways diseases.

The corresponding maleate salt of the compound of formula II, namely (R)-5-[2-(5,6-diethyl-indan-2-ylamino)-1-hydroxyethyl]-8-hydroxy-1H-quinolin-2-one maleate, has tested favourably in the clinic for the treatment of asthma and chronic obstructive pulmonary disease. Alternative salts have been investigated to address issues noted in formulating the compound for administered by inhalation, or at least provide a useful alternative to maleate salts.

Surprisingly, compounds of formula I have been found to present a good crystallinity and retain minimal residual solvent. They have low solubility in ethanol which is especially advantageous in inhalation products that contain ethanol. Agents of the invention may prevent or minimise the cough that certain patients have exhibited on administration, particularly first administration, of (R)-5-[2-(5,6-diethyl-indan-2-ylamino)-1-hydroxyethyl]-8-hydroxy-1H-quinolin-2-one maleate. Glycolate salts of formula I, including (R)-5-[2-(5,6-diethyl-indan-2-ylamino)-1-hydroxyethyl]-8-hydroxy-1H-quinolin-2-one glycolate, have been found to present a good crystallinity and is anhydrous. They are substantially not hydroscopic and have a clear melting peak at 140-250° C. They are especially stable, before and after micronisation, with or without excipients, and with and without moisture. They have low solubility in ethanol which is especially advantageous in inhalation products that contain ethanol. They also has good melting onset, no presence of residual solvent, a good crystallinity and no change of crystalline form after equilibration for 1 day at 25° C. in water, ethanol and isopropanol. Acetate salts of formula I, including (R)-5-[2-(5,6-diethyl-indan-2-ylamino)-1-hydroxyethyl]-8-hydroxy-1H-quinolin-2-one acetate, have been found to present a good crystallinity and retain minimal residual solvent. They are substantially not hydroscopic and have a clear melting peak at 140-250° C. They are especially stable, before and after micronisation, with or without excipients, and with and without moisture. They have low solubility in ethanol which is especially advantageous in inhalation products that contain ethanol. They also has good melting onset, no presence of residual solvent, and no change of crystalline form after equilibration for 1 day at 25° C. in water, ethanol and isopropanol. Xinafoate salts of formula I, including (R)-5-[2-(5,6-diethyl-indan-2-ylamino)-1-hydroxyethyl]-8-hydroxy-1H-quinolin-2-one xinafoate, have been found to present a good crystallinity and retain minimal residual solvent. They are substantially not hydroscopic and have a clear melting peak at 140-250° C. They are especially stable, before and after micronisation, with or without excipients, and with and without moisture. They have low solubility in ethanol which is especially advantageous in inhalation products that contain ethanol. They also has good melting onset, no presence of residual solvent, and no change of crystalline form after equilibration for 1 day at 25° C. in water, ethanol and isopropanol. Malonate salts of formula I, including (R)-5-[2-(5,6-diethyl-indan-2-ylamino)-1-hydroxyethyl]-8-hydroxy-1H-quinolin-2-one hydrogen malonate, have been found to present a good crystallinity and retain minimal residual solvent. They are substantially not hydroscopic and have a clear melting peak at 140-250° C. They are especially stable, before and after micronisation, with or without excipients, and with and without moisture. They have low solubility in ethanol which is especially advantageous in inhalation products that contain ethanol. They also has good melting onset, no presence of residual solvent, and no change of crystalline form after equilibration for 1 day at 25° C. in water, ethanol and isopropanol.

Given their anti-inflammatory activity, the agents of the invention are useful in the treatment of inflammatory conditions, particularly inflammatory or obstructive airways diseases. Treatment in accordance with the invention may be symptomatic or prophylactic.

Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. cortico-steroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Other inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, the agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

The agents of the invention are also useful in the treatment of inflammatory conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory conditions of the skin.

The agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, diseases of the joints such as rheumatoid arthritis and inflammatory bowel disease such as ulcerative colitis and Crohn's disease.

Further, agents of the invention may also be used for the treatment of cystic fibrosis, pulmonary hypertension and pulmonary fibrosis.

The agents of the invention are also useful as co-therapeutic agents for use in conjunction with other drug substances for treatment of airways diseases, particularly anti-inflammatory, bronchodilatory, antihistaminic/anti-allergic or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. The agents of the invention may be mixed with one, two, three or more other drugs in a fixed pharmaceutical composition or they may be administered separately, before, simultaneously with or after the other drug(s).

Such anti-inflammatory drugs include steroids, in particular glucocorticosteroids such as budesonide, beclamethasone dipropionate, fluticasone propionate, ciclesonide, dexamethasone, flunisolide, mometasone furoate and triamcinolone but also compounds described in WO 02/00679, WO 02/88167, WO 02/12266, WO 02/100879 or WO 02/00679, especially those of Examples 3, 11, 14, 17, 19, 26, 34, 37, 39, 51, 60, 67, 72, 73, 90, 99 and 101, (including salts or derivatives thereof such as sodium salts, sulphobenzoates, phosphates, isonicotinates, acetates, propionates, dihydrogen phosphates, palmitates, pivalates or furoates, and, where possible, hydrates) and non-steroidal steroid agonists such as those described in WO 00/00531, WO 02/10143, WO 03/082280, WO 03/082787, WO 03/104195, WO 04/005229; dopamine agonists such as bromocriptine, cabergolin, alpha-dihydroergocryptine, lisuride, pergolide, pramipexol, roxindol, ropinirol, talipexol, tergurid and viozan (including pharmaceutically acceptable salts thereof such as salts of hydrochloric acid, hydrobromic acid, sulphuric acid, phosphoric acid, methanesulphonic acid, acetic acid, fumaric acid, succinic acid, lactic acid, citric acid, tartaric acid and maleic acid); LTB4 antagonists such as BIIL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700 and WO 04/108720; LTD4 antagonists such as montelukast, pranlukast, zafirlukast, accolate, SR2640, Wy-48,252, ICI 198615, MK-571, LY-171883, Ro 24-5913 and L-648051; dopamine receptor agonists such as cabergoline, bromocriptine, ropinirole and 4-hydroxy-7-[2-[[2-[[3-(2-phenylethoxy)-propyl]sulfonyl]ethyl]-amino]ethyl]-2 (3H)-benzothiazolone and pharmaceutically acceptable salts thereof (the hydrochloride being Viozan®-AstraZeneca); PDE4 inhibitors such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID (TM) CC-10004 (Celgene), VM554/UM565 (Vernalis), T-440 (Tanabe), KW-4490 (Kyowa Hakko Kogyo), GRC 3886 (Oglemilast, Glenmark), WO 92/19594, WO 93/19749, WO 93/19750, WO 93/19751, WO 98/18796, WO 99/16766, WO 01/13953, WO 03/39544, WO 03/104204, WO 03/104205, WO 04/000814, WO 04/000839 and WO 04/005258 (Merck), WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607, WO 04/037805, WO 04/063197, WO 04/103998, WO 04/111044, WO 05/012252, WO 05012253, WO 05/013995, WO 05/030212, WO 05/030725, WO 05/087744, WO 05/087745, WO 05/087749 and WO 05/090345 (including physiologically acceptable acid addition salts thereof such as salts of hydrochloric acid, hydrobromic acid, sulphuric acid, phosphoric acid, methane-sulphonic acid, acetic acid, fumaric acid, succinic acid, lactic acid, citric acid, tartaric acid and maleic acid); A2a agonists such as those described in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; and A2b antagonists such as those described in WO 02/42298 and WO 03/042214.

Such bronchodilatory drugs include anticholinergic or antimuscarinic agents, in particular ipratropium bromide, oxitropium bromide, tiotropium salts, glycopyrrolate, CHF 4226 (Chiesi) and SVT-40776, but also those described in EP 424021, U.S. Pat. Nos. 3,714,357, 5,171,744, US 2005/171147, US 2005/182091, WO 01/04118, WO 02/00652, WO 02/51841, WO 02/53564, WO 03/00840, WO 03/33495, WO 03/53966, WO 03/87094, WO 04/18422, WO 04/05285, WO 04/96800, WO 05/77361 and WO 06/48225.

Suitable bronchodilatory also include beta-2 adrenoceptor agonists such as albuterol (salbutamol), metaproterenol, terbutaline, salmeterol, fenoterol, procaterol, and especially, formoterol, carmoterol, TA-2005, GSK159797 and pharmaceutically acceptable salts thereof, and also compounds of EP 147719, EP 1440966, EP 1460064, EP 1477167, EP 1574501, JP 05025045, JP 2005187357, US 2002/0055651, US 2004/0242622, US 2004/0229904, US 2005/0133417, US 2005/5159448, US 2005/5159448, US 2005/171147, US 2005/182091, US 2005/182092, US 2005/209227, US 2005/256115, US 2005/277632, US 2005/272769, US 2005/239778, US 2005/215542, US 2005/215590, US 2006/19991, US 2006/58530, WO 93/18007, WO 99/64035, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/16601, WO 04/22547, WO 04/32921, WO 04/33412, WO 04/37768, WO 04/37773, WO 04/37807, WO 04/39762, WO 04/39766, WO 04/45618 WO 04/46083, WO 04/80964, WO 04/087142, WO 04/89892, WO 04/108675, WO 04/108676, WO 05/33121, WO 05/40103, WO 05/44787, WO 05/58867, WO 05/65650, WO 05/66140, WO 05/70908, WO 05/74924, WO 05/77361, WO 05/90288, WO 05/92860, WO 05/92887, WO 05/90287, WO 05/95328, WO 05/102350, WO 06/56471, WO 06/74897 or WO 06/8173.

Suitable dual anti-inflammatory and bronchodilatory drugs include dual beta-2 adrenoceptor agonist/muscarinic antagonists such as those disclosed in US 2004/0167167, US 2004/0242622, US 2005/182092, US 2005/256114, US 2006/35933, WO 04/74246, WO 04/74812, WO 04/89892 and WO 06/23475.

Suitable antihistaminic/anti-allergic drug substances include acetaminophen, activastine, astemizole, azelastin, bamipin, cetirizine hydrochloride, cexchlorpheniramine, chlorophenoxamine, clemastine fumarate, desloratidine, dimenhydrinate, dimetinden, diphenhydramine, doxylamine, ebastine, emedastin, epinastine, fexofenadine hydrochloride, ketotifen, levocetirizine, levocabastin, loratidine, meclizine, mizolastine, pheniramine, promethazine and tefenadine, as well as those disclosed in JP 2004107299, WO 03/099807 and WO 04/026841 (including any pharmacologically acceptable acid addition salts thereof which may exist).

Combinations of the agents of the invention and steroids, PDE4 inhibitors or LTD4 antagonists are particularly suitable for use in the treatment of asthma. Whereas combinations of the agents of the invention and anticholinergic or antimuscarinic agents, PDE4 inhibitors, LTB4 antagonists are particularly suitable for use in the treatment of COPD.

In accordance with the foregoing, the invention provides a method for the treatment of an inflammatory condition, particularly an inflammatory or obstructive airways disease, which comprises administering to a subject, particularly a human subject, in need thereof an effective amount of a compound of formula I as hereinbefore described. The invention also provides the use of a compound of formula I as hereinbefore described for the manufacture of a medicament for the treatment of an inflammatory condition, particularly an inflammatory or obstructive airways disease.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

Accordingly the invention provides a pharmaceutical composition comprising as active ingredient a compound of formula I, optionally together with a pharmaceutically acceptable diluent or carrier therefor. The invention also provides a pharmaceutical composition comprising as active ingredient a compound of formula I and one, two, three or more anti-inflammatory, bronchodilatory, antihistaminic/anti-allergic or anti-tussive drug substances, optionally together with a pharmaceutically acceptable diluent or carrier therefor. Such compositions may be prepared using conventional diluents or excipients and techniques known in the galenic art.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof. Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, an agent of the invention having a particle diameter up to 10 microns, optionally together with a diluent or carrier, such as lactose, of the desired particle size distribution and a compound that helps to protect against product performance deterioration due to moisture e.g. magnesium stearate, typically 0.05-2.0% magnesium stearate. When the composition comprises a nebulised formulation, it preferably contains, for example, an agent of the invention either dissolved, or suspended, in a vehicle containing water, a co-solvent such as ethanol or propylene glycol and a stabiliser, which may be a surfactant.

The invention includes (A) an agent of the invention in inhalable form, e.g. in an aerosol or other atomisable composition or in inhalable particulate, e.g. micronised, form, (B) an inhalable medicament comprising an agent of the invention in inhalable form; (C) a pharmaceutical product comprising an agent of the invention in inhalable form in association with an inhalation device; and (D) an inhalation device containing an agent of the invention in inhalable form.

A suitable device for delivery of dry powder in encapsulated form is described in U.S. Pat. No. 3,991,761 (including the AEROLIZER™ device) or WO 05/113042, while suitable MDDPI devices include those described in WO 97/20589 (including the CERTIHALER™ device), WO 97/30743 (including the TWISTHALER™ device) and WO 05/37353 (including the GYROHALER™ device).

Dosages of agents of the invention employed in practising the present invention will of course vary depending, for example, on the particular condition to be treated, the effect desired and the mode of administration. In general, suitable daily dosages for administration by inhalation are of the order of 0.005 to 10 mg, while for oral administration suitable daily doses are of the order of 0.05 to 100 mg.

The invention is illustrated by the following Examples.

EXAMPLES

Example 1

Preparation of (R)-5-[2-(5,6-diethyl-indan-2-ylamino)-1-hydroxyethyl]-8-hydroxy-1H-quinolin-2-one hydrogen succinate

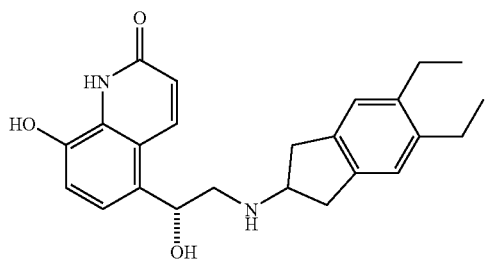

-continued

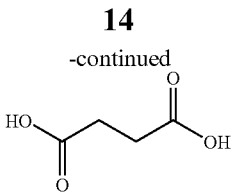

A suspension of 2.312 g (R)-5-[2-(5,6-diethyl-indan-2-ylamino)-1-hydroxyethyl]-8-hydroxy-1H-quinolin-2-one base (5.890 mmoles) and 0.695 g succinic acid (5.890 mmoles) in 50 ml isopropanol is heated to 80° C. The resulting almost clear solution is stirred at 80° C. Crystallization takes place spontaneously after ca. 5 minutes. The suspension is allowed to cool slowly and stirred at room temperature for 18 hours. The salt is collected after filtration and washing with 7 ml isopropanol. The crystals are dried for 20 hours at 70° C. and ca. 10 mbar.

Yield: 2.89 g white powder (96.3%)
Elemental Analysis:
Calc.: 65.87% C, 6.71% H, 5.49% N, 21.93% O.
Found: 65.49% C, 6.75% H, 5.56% N, 21.86% O.

Example 2

Preparation of (R)-5-[2-(5,6-diethyl-indan-2-ylamino)-1-hydroxyethyl]-8-hydroxy-1H-quinolin-2-one fumarate

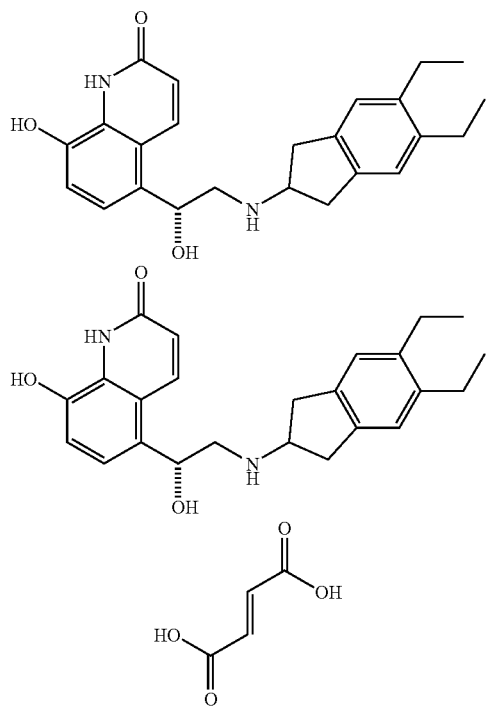

A suspension of 2.208 g (R)-5-[2-(5,6-diethyl-indan-2-ylamino)-1-hydroxyethyl]-8-hydroxy-1H-quinolin-2-one base (5.625 mmoles) in 20 ml methanol is heated to 50° C. A solution of 0.326 g fumaric acid (2.81 mmoles) in 5 ml methanol is dropwise added to the suspension at constant flow rate, over 10 minutes. The resulting solution is stirred at 50° C. Crystallization takes then spontaneously place after ca. 10 minutes. The suspension is allowed to cool and stirred for 3 hours at room temperature. The mixture is filtered. The crystals are washed with 7 ml methanol and dried first for 20 hours at 60° C. and ca. 10 mbar and further for 2 h at 60° C. and ca. 1 mbar. Yield: 2.19 g white powder (86.4%)

Elemental Analysis:
Calc.: 69.31% C, 6.71% H, 6.22% N, 17.76% O.
Found: 67.69% C, 6.62% H, 6.35% N, 19.00% O.

Example 3

Preparation of (R)-5-[2-(5,6-diethyl-indan-2-ylamino)-1-hydroxyethyl]-8-hydroxy-1H-quinolin-2-one hippurate

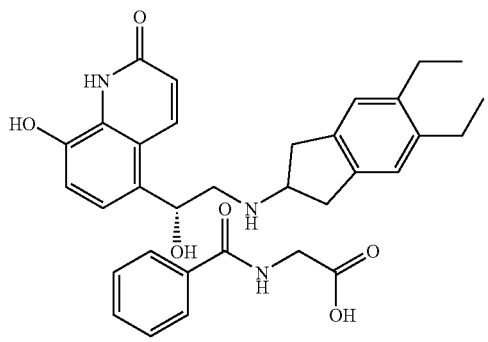

A suspension of 1.95 g (R)-5-[2-(5,6-diethyl-indan-2-ylamino)-1-hydroxyethyl]-8-hydroxy-1H-quinolin-2-one base (4.968 mmoles) in 28.5 ml methanol is heated to 45° C. 0.89 g hippuric acid (4.968 mmoles) are added in portions over 5 minutes at 45-50° C. The resulting almost complete solution, is further stirred at 50° C. Spontaneous crystallization occurs after ca 5 minutes. 15 ml methanol are added to the very thick mixture. The suspension is allowed to cool and stirred for 4 hours at room temperature. The suspension is filtered and the salt is washed with 10 ml methanol. The crystals are dried first for 20 hours at 70° C. and ca. 10 mbar and further for 4 hours at 60° C. and ca. 1 mbar. Yield: 2.15 g white powder (75.7%)

Elemental Analysis:
Calc.: 69.33% C, 6.52% H, 7.35% N, 16.79% O.
Found: 69.20% C, 6.67% H, 7.35% N, 16.85% O.

Example 4

Preparation of (R)-5-[2-(5,6-diethyl-indan-2-ylamino)-1-hydroxyethyl]-8-hydroxy-1H-quinolin-2-one mesylate monohydrate

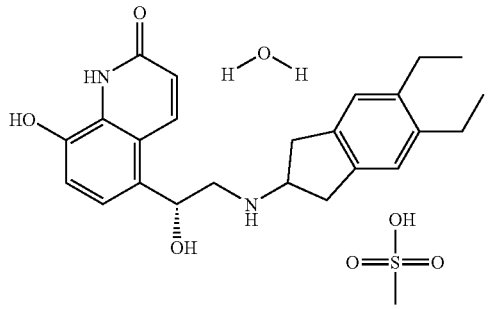

A suspension of 2.139 g (R)-5-[2-(5,6-diethyl-indan-2-ylamino)-1-hydroxyethyl]-8-hydroxy-1H-quinolin-2-one base (5.45 mmoles) in 20 ml water is heated to 70° C. A solution of 0.524 g methanesulfonic acid (5.45 mmoles) in 5 ml water is added dropwise over ca. 2 minutes. At the end of the addition the not dissolved solid consists of aggregates. A white good stirrable suspension is then formed after ca. 10 minutes. at 70° C. The mixture is slowly cooled to 25° C. and stirred for 20 hours at room temperature. After filtration, the solid is washed with 5 ml water and 10 ml acetone and dried for 20 hours at 70° C. and ca. 10 mbar. Yield: 2.40 g white powder (86.9%)

Elemental Analysis:
Calc.: 59.27% C, 6.76% H, 5.53% N, 6.33% S, 22.11% O.
Found: 59.24% C, 6.74% H, 5.46% N, 6.33% S, 22.36% O.
Water assay: 3.7% (m/m)

Example 5

Preparation of (R)-5-[2-(5,6-diethyl-indan-2-ylamino)-1-hydroxyethyl]-8-hydroxy-1H-quinolin-2-one hydrogen sulfate

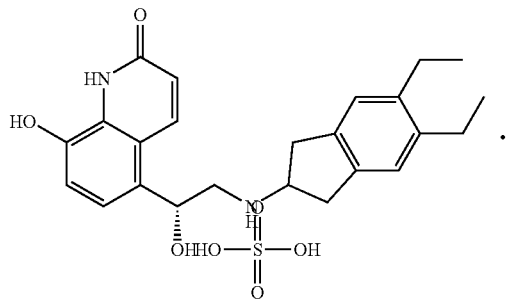

2.063 g (R)-5-[2-(5,6-diethyl-indan-2-ylamino)-1-hydroxyethyl]-8-hydroxy-1H-quinolin-2-one base (5.256 mmoles) are dissolved in 12 ml acetic acid at 50° C. A solution of 0.526 g sulfuric acid 98% (5.256 mmoles) in 4 ml acetic acid is adder dropwise, at constant flow rate, over 5 minutes. The clear solution is allowed to cool. Crystallization takes spontaneously place at ca. 35° C. The suspension is stirred for 18 h at room temperature and then filtered. The crystals are washed with 4 ml acetic acid and 10 ml ethylacetate. The salt is dried first for 20 hours at 70° C. and ca. 10 mbar and then for 2 hours at 60° C. and ca. 1 mbar. Yield: 2.31 g white powder (86.9%)

Elemental Analysis:
Calc.: 58.76% C, 6.16% H, 5.71% N, 6.54% S, 22.83% O.
Found: 57.22% C, 6.05% H, 5.31% N, 6.69% S, 24.55% O.

Example 6

Preparation of (R)-5-[2-(5,6-diethyl-indan-2-ylamino)-1-hydroxyethyl]-8-hydroxy-1H-quinolin-2-one hydrogen tartrate

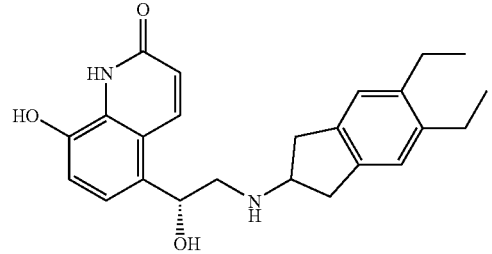

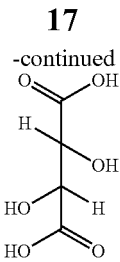

A suspension of 2.0 g (R)-5-[2-(5,6-diethyl-indan-2-ylamino)-1-hydroxyethyl]-8-hydroxy-1H-quinolin-2-one base (5.10 mmoles) in 14 ml isopropanol is heated at 50° C. Then a solution of 0.77 g L (+) tartaric acid (5.10 mmoles) in 7.7 ml isopropanol is dropwise added over ca. 2 minutes. The suspension is stirred at 50° C. for 15 hours. The white suspension is cooled to ca. 25° C. and filtered. The salt is washed with 10 ml isopropanol and dried for 18 hours/50° C./ca. 10 mbar and for 2 hours at 60° C./ca. 1 mbar. Yield: 2.33 g white powder (84.27%)

Elemental Analysis:

Calc.: 61.98% C, 6.32% H, 5.16% N, 26.54% O.

Found: 59.02% C, 6.41% H, 5.47% N, 23.30% O.

Example 7

Preparation of (R)-5-[2-(5,6-diethyl-indan-2-ylamino)-1-hydroxyethyl]-8-hydroxy-1H-quinolin-2-one hydrochloride

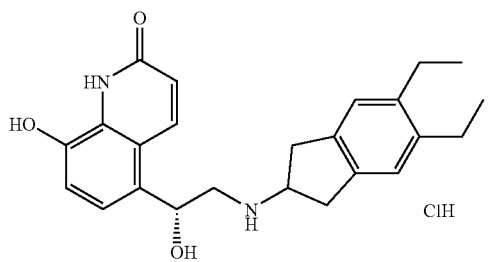

A suspension of 3.78 g (R)-5-[2-(5,6-diethyl-indan-2-ylamino)-1-hydroxyethyl]-8-hydroxy-1H-quinolin-2-one base (9.63 mmoles) in 36.5 ml methanol is heated to 50° C. A solution of 0.949 g hydrochloric acid 37% (9.63 mmoles) in 10 ml methanol is added dropwise, over 15 minutes. The resulting clear solution is allowed to cool. Crystallization begins spontaneously at 40° C. The suspension is stirred at room temperature for 17 hours. After filtration the salt is washed with 7 ml methanol. The crystals are dried for 16 hours at 50° C./ca. 10 mbar and for 2 hours at 50° C. and ca. 1 mbar. Yield: 2.33 g white powder (84.27%)

Elemental Analysis:

Calc.: 67.20% C, 6.81% H, 6.53% N, 8.26% Cl, 11.19% O.

Found: 66.79% C, 6.88% H, 6.55% N, 7.99% Cl, 11.81% O.

Example 8

Preparation of (R)-5-[2-(5,6-diethyl-indan-2-ylamino)-1-hydroxyethyl]-8-hydroxy-1H-quinolin-2-one hydrobromide

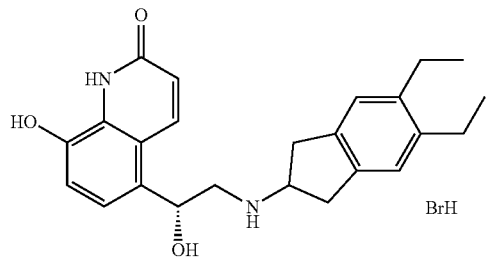

A suspension of 1.93 g (R)-5-[2-(5,6-diethyl-indan-2-ylamino)-1-hydroxyethyl]-8-hydroxy-1H-quinolin-2-one base (4.92 mmoles) in 13.5 ml methanol is heated to 50° C., A solution of 0.829 g hydrobromic acid 48% (4.92 mmoles) in 5 ml methanol is dropwise added over 15 minutes. The resulting very thick suspension is diluted with 43 ml methanol and allowed to cool. After stirring for 3 hours at room temperature the precipitate is filtered. The filter cake is washed with 5 ml methanol. The crystals are dried for 16 hours at 50° C./ca. 10 mbar and for 2 hours at 50° C. and ca. 1 mbar. Yield: 2.33 g white powder (84.27%)

Elemental Analysis:

Calc.: 60.89% C, 6.17% H, 5.92% N, 16.88% Br, 10.14% O.

Found: 60.55% C, 6.09% H, 6.00% N, 16.37% Br, 10.43% O.

Example 9

Preparation of (R)-5-[2-(5,6-diethyl-indan-2-ylamino)-1-hydroxyethyl]-8-hydroxy-1H-quinolin-2-one formate

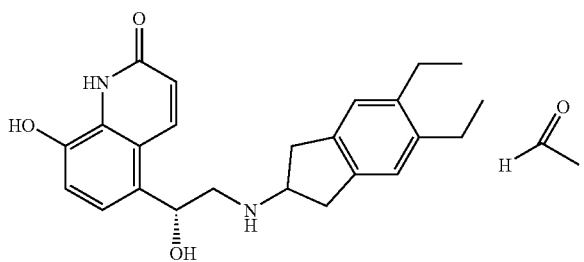

A suspension of 2.00 g (R)-5-[2-(5,6-diethyl-indan-2-ylamino)-1-hydroxyethyl]-8-hydroxy-1H-quinolin-2-one base (5.1 mmoles) in 15 ml methanol is heated to 50° C. 0.24 g formic acid (5.2 mmoles) are dropwise added. The dropping funnel is rinsed with 5 ml methanol. The resulting clear solution is allowed to slowly cool. Crystallization starts spontaneously at ca. 47° C. The mixture is stirred at ca. 25° c. for 15 hours and filtered. The filter cake is washed with 4 ml methanol. The salt is dried for 20 hours at 50° C./ca. 10 mbar and for 3 hours at 70° C. and ca. 1 mbar. Yield: 1.77 g white powder (79.37%)

Elemental Analysis:
Calc.: 68.47% C, 6.90% H, 6.39% N, 18.24% O.
Found: 68.30% C, 6.96% H, 6.38% N, 18.46% O.

Example 10

Preparation of (R)-5-[2-(5,6-diethyl-indan-2-ylamino)-1-hydroxyethyl]-8-hydroxy-1H-quinolin-2-one esylate

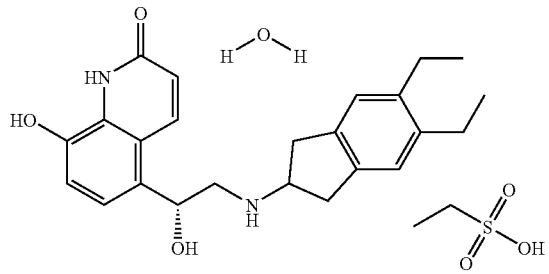

2.00 g (R)-5-[2-(5,6-diethyl-indan-2-ylamino)-1-hydroxyethyl]-8-hydroxy-1H-quinolin-2-one base (5.1 mmoles) are dissolved in 8 ml dimethylsulfoxide at 50° C. The solution is cooled to 25° C. 0.595 g ethanesulfonic acid (5.4 mmoles) are added dropwise over 5 minutes. and the dropping funnel is rinsed with 1 ml DMSO. Then 18 ml water are added at constant flow rate, over ca. 30 min. The resulting thick suspension is diluted with 8 ml water and stirred over night at room temperature. The mixture is filtered and the solid washed with 10 ml water. The product is dried for 3 hours at 50° C./ca. 10 mbar and for 3 hours at 70° C. and ca. 1 mbar.

Yield: 1.56 g white powder, Karl Fischer: 3.2% m/m H$_2$O
Elemental analysis: (calc. for the monohydrate)
Calc.: 59.98% C, 6.97% H, 5.38% N, 6.16% S, 21.51% O.
Found: 61.70% C, 6.73% H, 5.69% N, 6.36% S, 19.13% O.

Example 11

Preparation of (R)-5-[2-(5,6-diethyl-indan-2-ylamino)-1-hydroxyethyl]-8-hydroxy-1H-quinolin-2-one tosylate

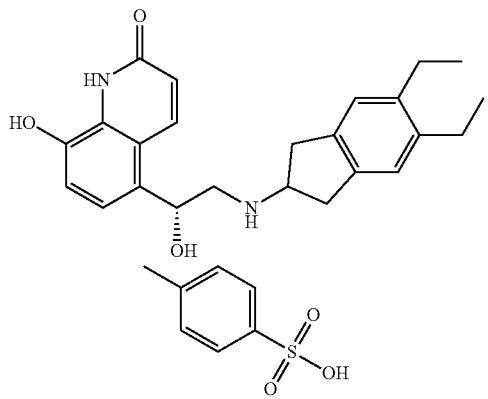

A mixture of 2.00 g (R)-5-[2-(5,6-diethyl-indan-2-ylamino)-1-hydroxyethyl]-8-hydroxy-1H-quinolin-2-one base (5.1 mmoles) and 0.98 g p-toluenesulfonic acid monohydrate (5.1 mmoles) in 30 ml ethylacetate is heated to 60° C. During heating the initially sticky yellow amorphous mass, turns to a white, good stirrable suspension. The suspension is allowed to cool and stirred at room temperature over night. The crystals are collected after filtration and washing with ethylacetate. The salt is dried for ca. 20 hours at 50° C. and ca. 10 mbar. Yield: 2.73 g off white powder (94.8%)

Elemental Analysis:
Calc.: 65.94% C, 6.43% H, 4.96% N, 5.68% S, 17.00% O.
Found: 64.51% C, 6.42% H, 5.01% N, 5.60% S, 18.60% O.

Example 12

Preparation of (R)-5-[2-(5,6-diethyl-indan-2-ylamino)-1-hydroxyethyl]-8-hydroxy-1H-quinolin-2-one glycolate

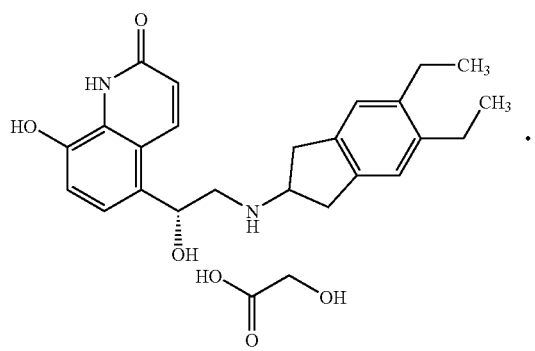

A suspension of 2.075 g (R)-5-[2-(5,6-diethyl-indan-2-ylamino)-1-hydroxyethyl]-8-hydroxy-1H-quinolin-2-one base (5.286 mmoles) in 25 ml methanol is heated to 50° C. A solution of 0.402 g glycolic acid (5.286 mmoles) in 5 ml methanol is added dropwise over 7 minutes. The resulting clear solution is stirred at 50° C. Crystallization takes spontaneously place after ca 15 minutes. The white suspension is allowed to cool to room temperature and stirred over night at ca. 25° C. After 18 hours the salt is filtered. The filter cake is washed with 7 ml methanol and dried first 20 hours at 60° C. and ca. 10 mbar and then 2 hours at 60° C. and ca. 1 mbar.

Yield: 1.77 g white powder (71.37%).
Elementary Analysis:
Calc.: 66.65% C, 6.88% H, 5.98% N, 20.49% O.
Found: 66.46% C, 6.80% H, 6.19% N, 20.33% O.

Example 13

Characterisation of Salt by X-Ray Powder Diffraction

The X-ray diffraction pattern of (R)-5-[2-(5,6-diethyl-indan-2-ylamino)-1-hydroxyethyl]-8-hydroxy-1H-quinolin-2-one glycolate prepared in accordance with Example 12 is measured using a SCINTAG™ X-ray diffractometer with a CuK alpha radiation source. The X-ray diffraction pattern thus determined is shown in FIG. 1 and represented in Table I below by the reflection lines and intensities of the most important lines.

TABLE I

X-ray diffraction lines and intensities for the glycolate salt

| 2θ (°) | d-spacings (Å) | Relative intensity |
|---|---|---|
| 2.8 | 31.28 | S |
| 5.7 | 15.39 | M |
| 12.2 | 7.22 | M |
| 14.5 | 6.10 | M |
| 15.2 | 5.84 | L |
| 16.8 | 5.27 | L |
| 17.4 | 5.08 | L |
| 18.3 | 4.82 | L |
| 19.2 | 4.62 | L |
| 19.7 | 4.51 | L |
| 20.4 | 4.35 | L |
| 21.4 | 4.14 | L |
| 23.3 | 3.82 | M |
| 25.4 | 3.50 | L |
| 26.4 | 3.38 | L |

The XRPD pattern shows a strong diffraction peak at 2.8°.

Example 14

Characterisation of Salt by IR Spectroscopy

Figure 2:
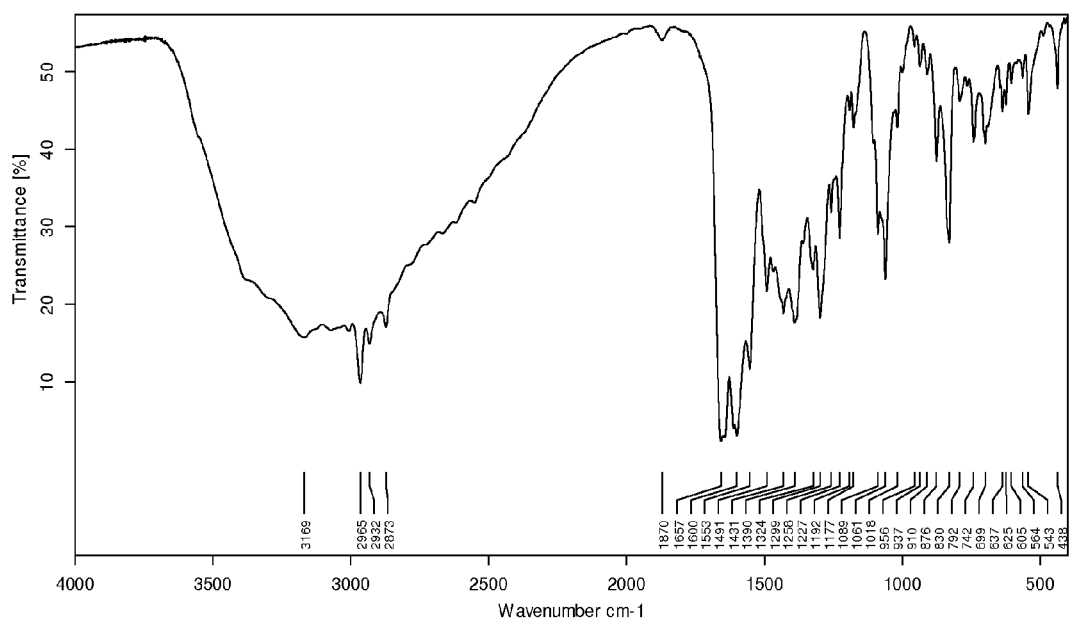

The IT-IR spectrum of (R)-5-[2-(5,6-diethyl-indan-2-ylamino)-1-hydroxyethyl]-8-hydroxy-1H-quinolin-2-one glycolate prepared in accordance with Example 12 is measured using the transmission KBr technique (in a KBr-disc with ca. 1.1/302 mg) and a BRUKER OPTICS IFS-55™ Fourier Transform Infrared (FTIR) spectrometer. The IT-IR spectrum thus determined is shown in FIG. 2. Major IR bands are recorded Main IR bands: 3169; 2965; 1657; 1599; 1552; 1491; 1431; 1390; 1298; 1226; 1088; 1061; 875; 829; 742; 699; 543 cm$^{-1}$.

Example 15

Preparation of (R)-5-[2-(5,6-diethyl-indan-2-ylamino)-1-hydroxyethyl]-8-hydroxy-1H-quinolin-2-one acetate

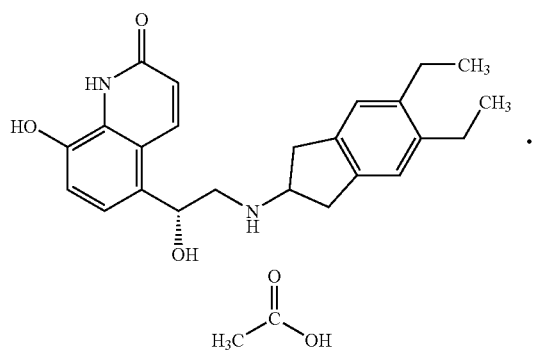

2.168 g (R)-5-[2-(5,6-diethyl-indan-2-ylamino)-1-hydroxyethyl]-8-hydroxy-1H-quinolin-2-one base (5.523 mmoles) and 1.17 g acetic acid (19.48 mmoles) are dissolved in 60 ml isopropanol at 80° C. The clear solution is allowed to cool slowly. Crystallization takes place spontaneously at 35° C. The suspension is stirred for 17 hours at room temperature and then filtered. The filter cake is washed with 10 ml isopropanol and dried at 60° C./ca 10 mbar for 20 hours.

Yield: 2.123 g white crystals (84.9%)

Elemental Analysis:

Calc.: 69.01% C, 7.13% H, 6.19% N, 17.68% O.

Found: 68.92% C, 6.98% H, 6.12% N, 17.67% O.

Example 16

Characterisation of Salt by X-Ray Powder Diffraction

Figure 3:
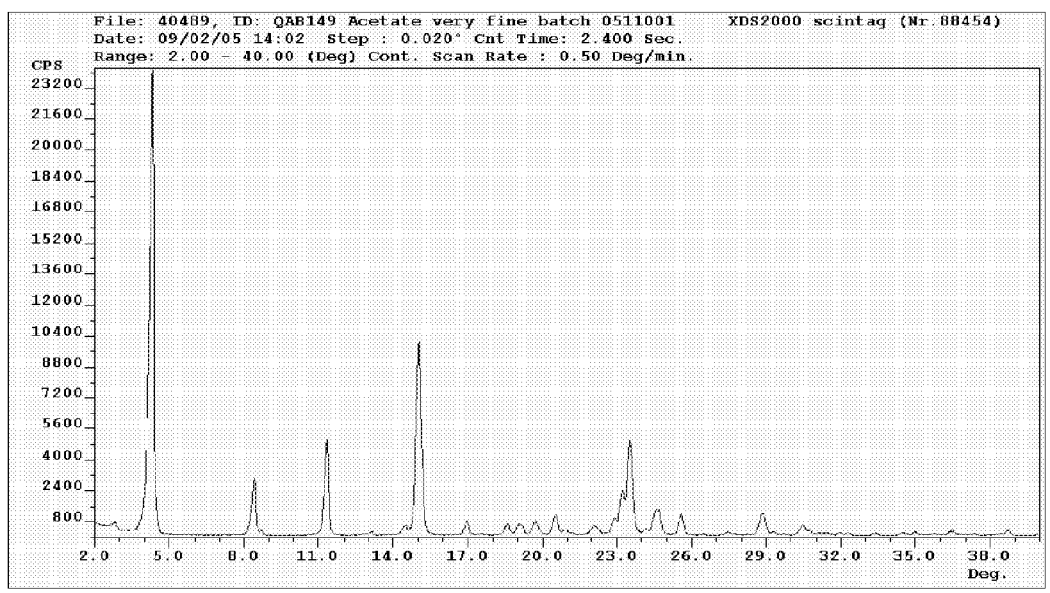

The X-ray diffraction pattern of (R)-5-[2-(5,6-diethyl-indan-2-ylamino)-1-hydroxyethyl]-8-hydroxy-1H-quinolin-2-one acetate prepared in accordance with Example 15 is measured using a SCINTAG™ X-ray diffractometer with a CuK alpha radiation source. The X-ray diffraction pattern thus determined is shown in FIG. 3 and represented in Table II below by the reflection lines and intensities of the most important lines.

TABLE II

X-ray diffraction lines and intensities for the acetate salt

| 2θ (°) | d-spacings (Å) | Relative intensity |
|---|---|---|
| 4.3 | 20.36 | S |
| 8.4 | 10.48 | M |
| 11.4 | 7.78 | M |
| 15.1 | 5.88 | S |
| 17.0 | 5.21 | L |
| 18.6 | 4.76 | L |
| 19.1 | 4.64 | L |
| 19.7 | 4.49 | L |
| 20.5 | 4.32 | L |
| 22.9 | 3.87 | L |
| 23.3 | 3.82 | L |
| 23.5 | 3.78 | M |
| 24.6 | 3.61 | L |
| 25.6 | 3.48 | L |
| 28.9 | 3.09 | L |
| 30.5 | 2.93 | L |

The XRPD pattern shows a strong diffraction peak at 4.3°.

Example 17

Characterisation of Salt by IR Spectroscopy

Figure 4:
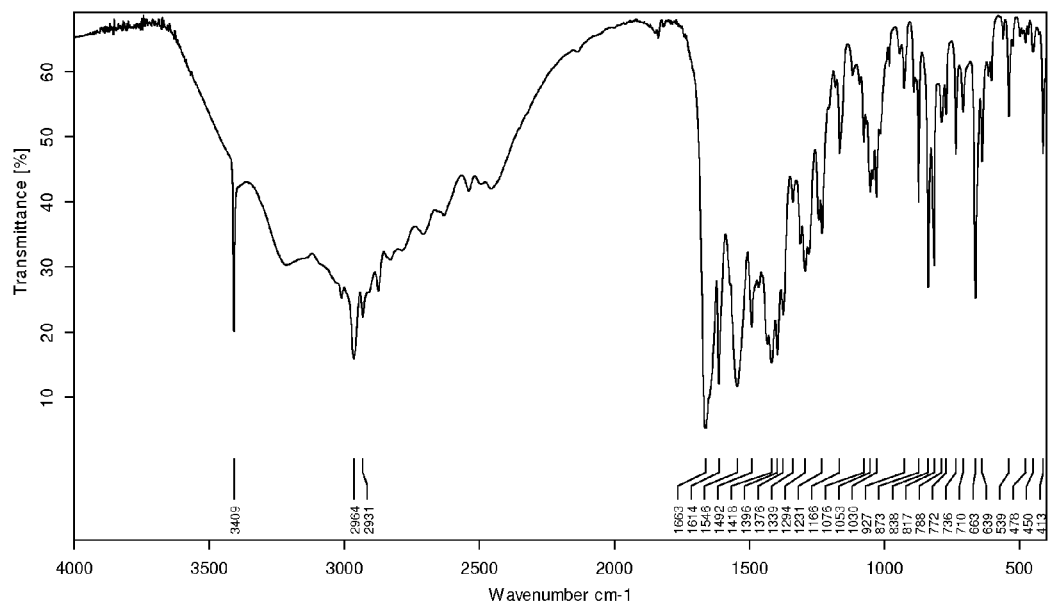

The IT-IR spectrum of (R)-5-[2-(5,6-diethyl-indan-2-ylamino)-1-hydroxyethyl]-8-hydroxy-1H-quinolin-2-one acetate prepared in accordance with Example 15 is measured using the transmission KBr technique (in a KBr-disc with ca. 1.1/300 mg) and a BRUKER OPTICS IFS-55™ Fourier Transform Infrared (FTIR) spectrometer. The IT-IR spectrum thus determined is shown in FIG. 4. Major IR bands are recorded Main IR bands: 3409; 2964; 1663; 1613; 1546; 1491; 1417; 1396; 1293; 1231; 1165; 1029; 873; 838; 816; 663 cm$^{-1}$.

Example 18

Preparation of (R)-5-[2-(5,6-diethyl-indan-2-ylamino)-1-hydroxyethyl]-8-hydroxy-1H-quinolin-2-one xinafoate

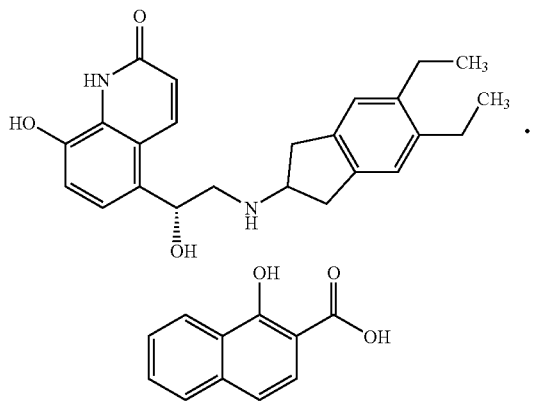

5.0 g (R)-5-[2-(5,6-diethyl-indan-2-ylamino)-1-hydroxyethyl]-8-hydroxy-1H-quinolin-2-one base (12.738 mmoles) and 2.40 g 1-hydroxy-2-naphthoic acid (12.626 mmoles) are dissolved in 60 ml n-butanol at 100° C. The solution is allowed to cool. Some seeds are added at 25° C. and crystallization takes place slowly. The suspension is stirred for 17 hours at room temperature and then filtered. The crystals are washed with 10 ml n-butanol and dried at 70° C. and ca. 10 mbar for 20 hours. Yield: 5.57 g beige powder (76%).

Elemental Analysis:
Calc.: 72.40% C, 6.25% H, 4.82% N, 16.53% O.
Found: 72.16% C, 6.18% H, 4.81% N, 16.47% O.

Example 19

Characterisation of Salt by X-Ray Powder Diffraction

Figure 5:
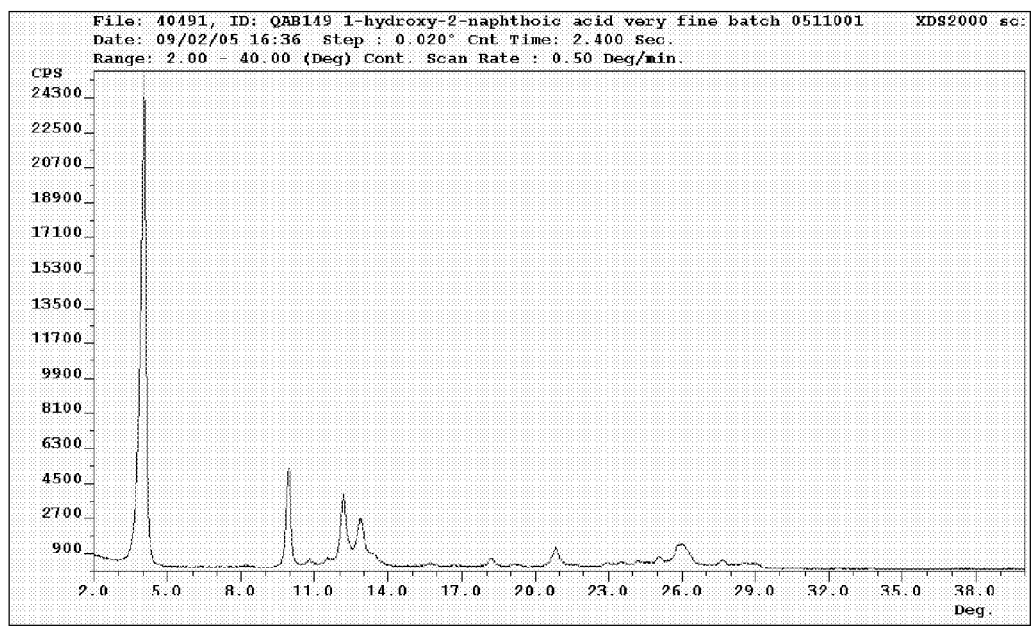

The X-ray diffraction pattern of (R)-5-[2-(5,6-diethyl-indan-2-ylamino)-1-hydroxyethyl]-8-hydroxy-1H-quinolin-2-one xinafoate prepared in accordance with Example 18 is measured using a SCINTAG™ X-ray diffractometer with a CuK alpha radiation source. The X-ray diffraction pattern thus determined is shown in FIG. 5 and represented in Table III below by the reflection lines and intensities of the most important lines.

TABLE III

X-ray diffraction lines and intensities for the xinafoate salt

| 2θ (°) | d-spacings (Å) | Relative intensity |
| --- | --- | --- |
| 4.1 | 21.72 | S |
| 10.0 | 8.87 | M |
| 12.2 | 7.25 | M |
| 12.9 | 6.85 | M |
| 18.2 | 4.86 | L |
| 20.9 | 4.25 | L |
| 25.9 | 3.43 | L |

The XRPD pattern shows a strong diffraction peak at 4.1°.

Example 20

Characterisation of Salt by IR Spectroscopy

Figure 6:
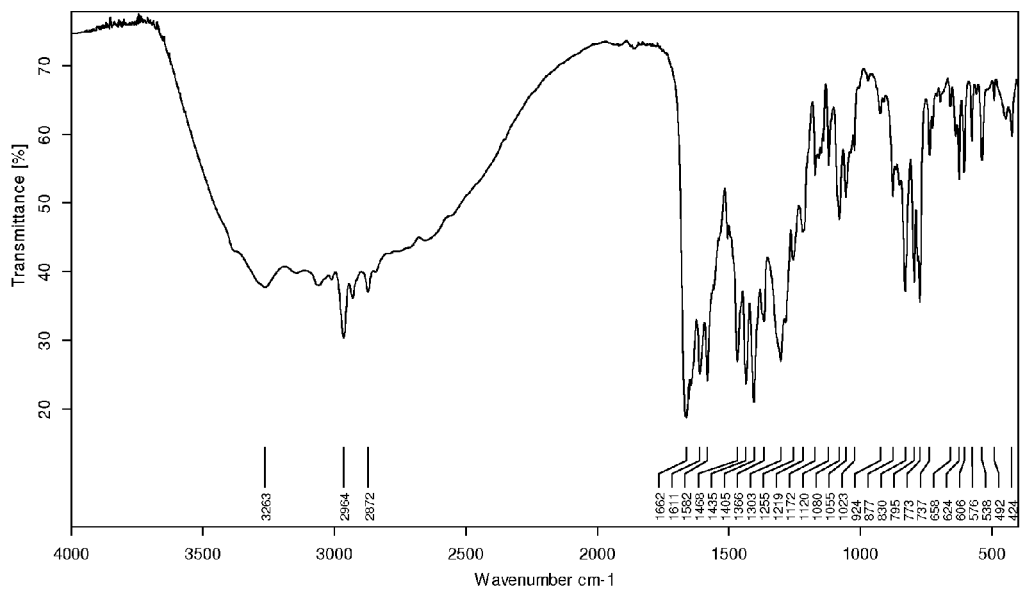

The IT-IR spectrum of (R)-5-[2-(5,6-diethyl-indan-2-ylamino)-1-hydroxyethyl]-8-hydroxy-1H-quinolin-2-one xinafoate prepared in accordance with Example 18 is measured using the transmission KBr technique (in a KBr-disc with ca. 1.2/305 mg) and a BRUKER OPTICS IFS-55™ Fourier Transform Infrared (FTIR) spectrometer. The IT-IR spectrum thus determined is shown in FIG. 6. Main IR bands: 2964; 1661; 1611; 1582; 1467; 1435; 1404; 1303; 1255; 1172; 1079; 1054; 829; 795; 773; 624; 537 cm$^{-1}$.

Example 21

Preparation of (R)-5-[2-(5,6-diethyl-indan-2-ylamino)-1-hydroxyethyl]-8-hydroxy-1H-quinolin-2-one hydrogen malonate

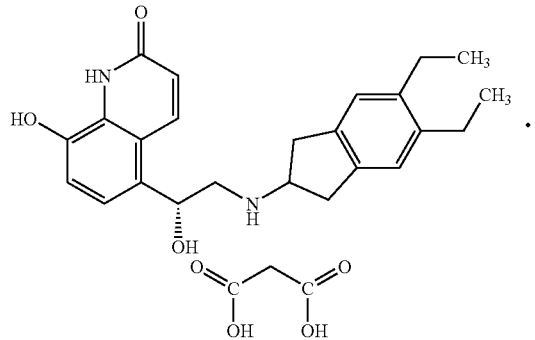

A suspension of 2.172 g (R)-5-[2-(5,6-diethyl-indan-2-ylamino)-1-hydroxyethyl]-8-hydroxy-1H-quinolin-2-one base (5.533 mmoles) und 0.576 g malonic acid (5.533 mmoles) in 25 ml n-butanol is heated to 80° C. Initially an oil formed during heating, which crystallizes on prolonged heating. The mixture is stirred at 80° C. for 15 minutes and then allowed to cool to room temperature. The suspension is stirred for 18 hours at room temperature. After filtration the crystals are washed with 5 ml n-butanol and 10 ml acetone. The product is dried at 70° C. and 70° C. for 20 hours. Yield: 2.62 g white powder (95.28%)

Elemental Analysis:
Calc.: 65.31% C, 6.50% H, 5.64% N, 22.55% O.
Found: 65.21% C, 6.50% H, 5.75% N, 22.49% O.

Example 22

Characterisation of Salt by X-Ray Powder Diffraction

Figure 7:
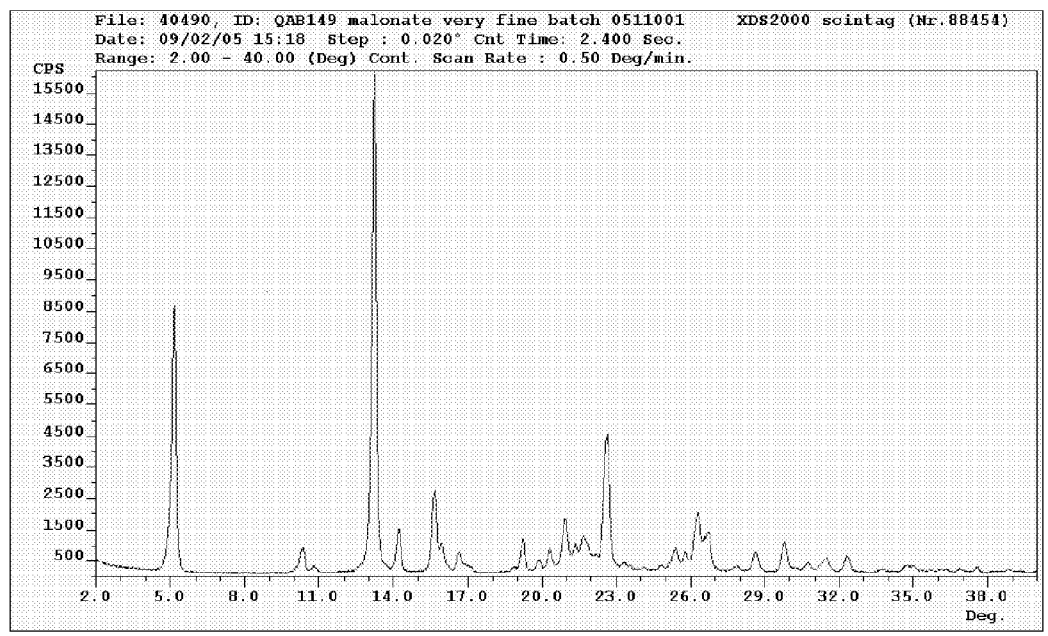

The X-ray diffraction pattern of (R)-5-[2-(5,6-diethyl-indan-2-ylamino)-1-hydroxyethyl]-8-hydroxy-1H-quinolin-2-one hydrogen malonate prepared in accordance with Example 21 is measured using a SCINTAG™ X-ray diffractometer with a CuK alpha radiation source. The X-ray diffraction pattern thus determined is shown in FIG. 7 and represented in Table IV below by the reflection lines and intensities of the most important lines.

TABLE IV

X-ray diffraction lines and intensities for the hydrogen malonate salt

| 2θ (°) | d-spacings (Å) | Relative intensity |
|---|---|---|
| 5.2 | 17.03 | S |
| 10.4 | 8.53 | L |
| 13.3 | 6.67 | S |
| 14.2 | 6.21 | M |
| 15.7 | 5.64 | M |
| 16.0 | 5.54 | L |
| 16.7 | 5.31 | L |
| 19.3 | 4.60 | M |
| 20.3 | 4.36 | L |
| 21.0 | 4.23 | M |
| 21.4 | 4.15 | L |
| 21.7 | 4.09 | L |
| 22.6 | 3.92 | M |
| 25.4 | 3.50 | L |
| 25.8 | 3.45 | L |
| 26.3 | 3.38 | M |
| 26.7 | 3.33 | L |
| 28.7 | 3.11 | L |
| 29.8 | 2.99 | L |
| 32.4 | 2.76 | L |

The XRPD pattern shows a strong diffraction peak at 13.3°.

Example 23

Characterisation of Salt by IR Spectroscopy

Figure 8:
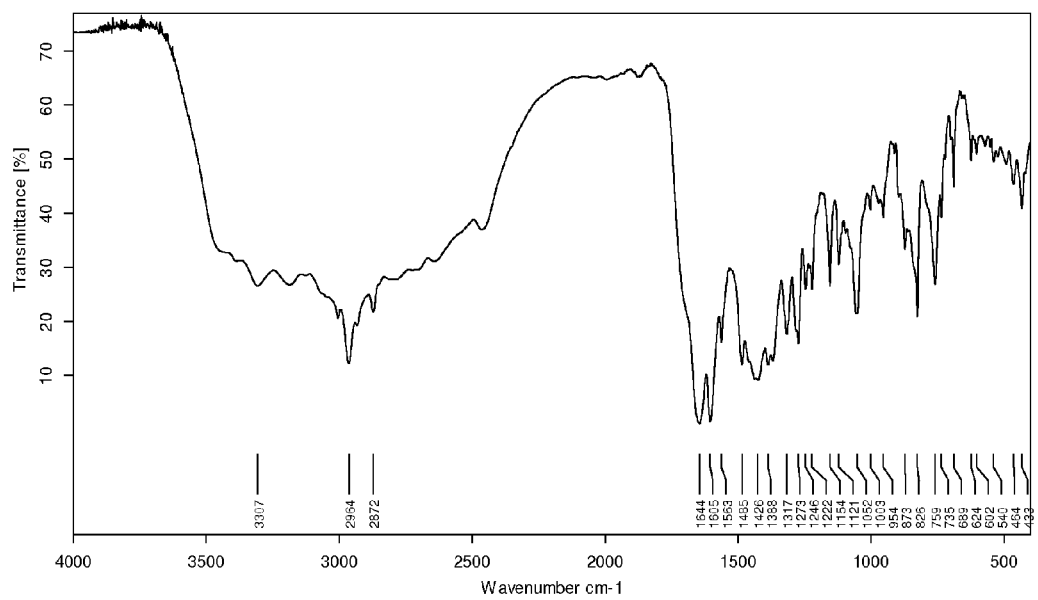

The IT-IR spectrum of (R)-5-[2-(5,6-diethyl-indan-2-ylamino)-1-hydroxyethyl]-8-hydroxy-1H-quinolin-2-one hydrogen malonate prepared in accordance with Example 21 is measured using the transmission KBr technique (in a KBr-disc with ca. 1.3/303 mg) and a BRUKER OPTICS IFS-55™ Fourier Transform Infrared (FTIR) spectrometer. The IT-IR spectrum thus determined is shown in FIG. 8. Main IR bands: 3306; 2964; 1644; 1604; 1563; 1484; 1426; 1387; 1317; 1272; 1154; 1051; 826; 758; 689 cm$^{-1}$.

The invention claimed is:

1. A compound that is (R)-5-[2-(5,6-diethyl-indan-2-ylamino)-1-hydroxyethyl]-8-hydroxy-1H-quinolin-2-one acetate having the following characteristic diffraction lines in the x-ray diffraction pattern thereof: 4.3°, 8.4°, 11.4°, 15.1°, 17.0°, 18.6°, 19.1°, 19,7°, 20.5°, 22.9°, 23.3°, 23.5°, 24.6°, 25.6°, 28.9° and 30.5°.

2. A pharmaceutical composition comprising, as active ingredient, an effective amount of a compound of claim 1, optionally together with a pharmaceutically acceptable carrier.

3. A pharmaceutical composition according to claim 2, which is in inhalable form.

4. A pharmaceutical composition according to claim 2, that further comprises as active ingredient one, two, three or more anti-inflammatory, bronchodilatory, antihistaminic/anti-allergic or anti-tussive drug substances.

5. A pharmaceutical composition according to claim 4, that further comprises as active ingredient one or both of mometasone furoate and glycopyrrolate.

6. A Method of treating an inflammatory or obstructive airway disease in a subject in need of such treatment, which comprises administering to said subject an effective amount of a compound as defined in claim 1.

7. A method of treating asthma in a subject in need of such treatment, which comprises administering to said subject an effective amount of a compound of formula I as defined in claim 1.

8. A method of treating chronic obstructive pulmonary disease in a subject in need of such treatment, which comprises administering to said subject an effective amount of a compound of formula I as defined in claim 1.

9. A compound that is (R)-5-[2-(5,6-diethyl-indan-2-ylamino)-1-hydroxyethyl]-8-hydroxy-1H-quinolin-2-one xinafoate having the following characteristic diffraction lines in the x-ray diffraction pattern thereof: 4.1°, 10.0°, 12.2°, 12.9°, 18.2°, 20.9° and 25.9°.

10. A pharmaceutical composition comprising active ingredient, an effective amount of a compound of claim 9, optionally together with a pharmaceutically acceptable carrier.

11. A pharmaceutical composition according to 10, which is in inhalable form.

12. A pharmaceutical composition according to claim 10, that further comprises as active ingredient one, two, three or more anti-inflammatory, bronchodilatory, antihistaminic/anti-allergic or anti-tussive drug substances.

13. A pharmaceutical composition according to claim 12, that further comprises as active ingredient one or both of mometasone furoate and glycopyrrolate.

14. A method of treating an inflammatory or obstructive airway disease in a subject in need of such treatment, which comprises administering to said subject effective amount of a compound as defined in claim 9.

15. A method of treating asthma in a subject in need of such treatment, which comprises administering to said subject an effective amount of a compound of formula I as defined in claim 9.

16. A method of treating chronic obstructive pulmonary disease in a subject in need of such treatment, which comprises administering to said subject an effective amount of a compound of formula I as defined in claim 6.

* * * * *